United States Patent
Asako et al.

(10) Patent No.: US 8,178,325 B2
(45) Date of Patent: May 15, 2012

(54) PROCESS FOR PRODUCING SULFUR-CONTAINING HYDROXYCARBOXYLIC ACID

(75) Inventors: Hiroyuki Asako, Toyonaka (JP); Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 357 days.

(21) Appl. No.: 12/440,621

(22) PCT Filed: Sep. 21, 2007

(86) PCT No.: PCT/JP2007/069126
§ 371 (c)(1),
(2), (4) Date: Mar. 10, 2009

(87) PCT Pub. No.: WO2008/038810
PCT Pub. Date: Apr. 3, 2008

(65) Prior Publication Data
US 2009/0275094 A1 Nov. 5, 2009

(30) Foreign Application Priority Data

Sep. 25, 2006 (JP) ................. 2006-258452
Jan. 23, 2007 (JP) ................. 2007-012349

(51) Int. Cl.
*C12P 11/00* (2006.01)
(52) U.S. Cl. ........ 435/130; 435/132; 435/148; 435/170; 435/253.3; 435/252.5
(58) Field of Classification Search .................. 435/130, 435/132, 148, 170, 253.3, 252.5
See application file for complete search history.

(56) References Cited

FOREIGN PATENT DOCUMENTS

EP         1 795 602 A    6/2007
WO        02/33110 A      4/2002

OTHER PUBLICATIONS

ATCC webpage for strain Norcardia globerula ATCC15076 http://www.atcc.org/ATCCAdvancedCatalogSearch/ProductDetails/tabid/452/Default.aspx?ATCCNum=15076&Template=bacteria downloaded Jun. 24, 2011.*
Database WPI Week 199213, Derwent Publications Ltd., London, GB; AN 1992-099665 (XP-002460361).

* cited by examiner

*Primary Examiner* — Susan Hanley
(74) *Attorney, Agent, or Firm* — Sughrue Mion, PLLC

(57) ABSTRACT

There is provided is a process for producing a sulfur-containing α-hydroxycarboxylic acid compound represented by the formula (2):

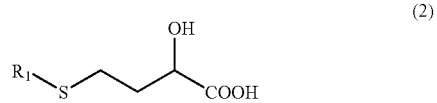

(2)

wherein $R_1$ represents hydrogen, $C_{1-8}$ alkyl, or $C_{6-20}$ aryl, which comprises subjecting a sulfur-containing ketol represented by the formula (1):

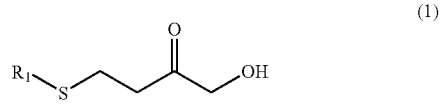

(1)

wherein $R_1$ is the same as defined above, to the action of microbial cells of a microorganism belonging to the genus *Pseudomonas*, *Rhodococcus* or *Bacillus* capable of converting the ketol into a corresponding α-hydroxycarboxylic acid compound, or a treated material thereof, thereby producing the sulfur-containing α-hydroxycarboxylic acid without using a hydroxynitrile compound as a starting material.

8 Claims, No Drawings

PROCESS FOR PRODUCING SULFUR-CONTAINING HYDROXYCARBOXYLIC ACID

CROSS-REFERENCE TO RELATED APPLICATIONS

This application is a U.S. National Phase application under 35 U.S.C. §371 of International Application No. PCT/JP07/69126, filed Sep. 21, 2007, claiming priority of Japanese Patent Application No. 2007-012349, filed on Jan. 23, 2007, and Japanese Patent Application No. 2006-258452, filed on Sep. 25, 2006 the entire contents of each of which are hereby incorporated by reference.

TECHNICAL FIELD

The present invention relates to a process for producing a sulfur-containing hydroxycarboxylic acid.

BACKGROUND ART

Hitherto, as a process for producing a sulfur-containing hydroxycarboxylic acid, hydrolysis of a hydroxynitrile compound (cyanhydrin) has been employed. Industrially, sulfuric acid is used as a catalyst. Further, for example, JP 58-15120 B, JP 2-84198 A and JP 4-40898 disclose hydrolysis of a hydroxynitrile compound by the action of a microorganism to convert it into a corresponding hydroxycarboxylic acid.

However, in a process using sulfuric acid as a catalyst, a hydroxynitrile compound is reacted with sulfuric acid to produce, in addition to the objective hydroxycarboxylic acid, an equimolar amount of ammonium sulfate as a by-product. Therefore, a step for recovering the by-product is required, which makes production steps complicated. Further, in a process for producing a hydroxycarboxylic acid compound from a corresponding hydroxynitrile compound by using a microorganism, there are such problems that the enzyme activity possessed by the microorganism is inhibited by degradation products from the hydroxynitrile compound, i.e., cyan, etc., and treatment of a large amount of an ammonium salt produced is required, thereby accompanying an increase in the production cost.

DISCLOSURE OF THE INVENTION

An object of the present invention is to provide a process for producing a sulfur-containing hydroxycarboxylic acid having no fear that a large amount of a by-product is produced, and the enzyme activity is inhibited.

That is, the present invention provides:

1. A process for producing a sulfur-containing α-hydroxycarboxylic acid compound represented by the formula (2):

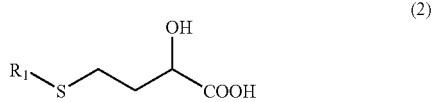

wherein $R_1$ represents a hydrogen atom, an alkyl group having 1 to 8 carbon atoms, or an aryl group having 6 to 20 carbon atoms, which comprises subjecting a sulfur-containing ketol represented by the formula (1):

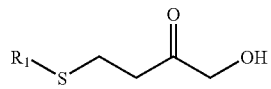

wherein $R_1$ is the same as defined above, to the action of microbial cells of a microorganism belonging to the genus *Pseudomonas*, *Rhodococcus* or *Bacillus* capable of converting the sulfur-containing ketol into a corresponding sulfur-containing α-hydroxycarboxylic acid compound, or a treated material thereof;

2. The process according to the above 1, wherein the microorganism is that belonging to the genus *Pseudomonas*, or *Rhodococcus* which has been cultured in the presence of a primary or secondary alcohol;

3. The process according to the above 1 or 2, wherein the microorganism is that belonging to *Pseudomonas putida*, *Pseudomonas diminuta*, *Pseudomonas mendocina*, *Rhodococcus globerulus*, *Rhodococcus erythropolis*, *Rhodococcus rhodochrous*, or *Rhodococcus* sp;

4. The process according to the above 1, wherein the microorganism is that belonging to *Bacillus alvei*;

5. The process according to any one of the above 1 to 3, wherein the microorganism is *Pseudomonas putida* IFO14164t, *Pseudomonas putida* IAM1236, *Pseudomonas diminuta* JCM2788t, *Pseudomonas mendocina* IFO14162, *Rhodococcus globerulus* ATCC15076, *Rhodococcus erythropolis* IFO12320, *Rhodococcus rhodochrous* ATCC15610, or *Rhodococcus* sp. ATCC19148;

6. The process according to the above 1 or 4, wherein the microorganism is *Bacillus alvei* IFO3343t;

7. The process according to any one of the above 1 to 6, wherein $R_1$ in the sulfur-containing ketol represented by the formula (1) is an alkyl group having 1 to 8 carbon atoms;

8. The process according to the above 2, wherein the primary or the secondary alcohol is a primary or secondary alcohol having 1 to 5 carbon atoms; and 9. The process according to the above 8, wherein the primary or the secondary alcohol is 1-propanol.

According to the present invention, a sulfur-containing hydroxycarboxylic acid compound can be efficiently produced without any fear that a large amount of a by-product is produced, and the enzyme activity is inhibited.

BEST MODE FOR PERFORMING THE INVENTION

Hereinafter, the process of the present invention will be explained.

In the sulfur-containing ketol represented by the formula (1), and the sulfur-containing hydroxycarboxylic acid compound represented by the formula (2), examples of the alkyl group of having 1 to 8 carbon atoms of $R_1$ include a methyl group, an ethyl group, a propyl group, an isopropyl group, a butyl group, an isobutyl group, a t-butyl group, a pentyl group, a hexyl group, a heptyl group, and an octyl group. Further, examples of the aryl group having 6 to 20 carbon atoms of $R_1$ include a phenyl group, a tolyl group, a xylyl group, a naphthyl group, and the like.

$R_1$ in the sulfur-containing ketol compound represented by the formula (1) is preferably an alkyl group having 1 to 8 carbon atoms.

The sulfur-containing hydroxycarboxylic acid compound represented by the formula (2) which is produced by the process of the present invention from the corresponding sulfur-containing ketol compound represented by the formula (1), and recovered from a reaction mixture may be in the form of a salt.

The compound of the formula (1) can be produced, for example, by a coupling reaction of 3-methylthiopropion-aldehyde and paraformaldehyde using a thiazolinium salt and a base as catalysts (for example, see Japanese Patent Application No. 2006-199127) or a similar reaction.

Microbial cells of a microorganism or a treated material thereof to be used as a catalyst in the process of the present invention may be any microbial cells or treated materials thereof as far as they are microbial cells of a microorganism belonging to the genus *Pseudomonas, Rhodococcus* or *Bacillus* capable of converting a sulfur-containing ketol into a corresponding sulfur-containing α-hydroxycarboxylic acid, and treated materials thereof. Examples thereof include microbial cells or treated materials of a microorganism belonging to the genus *Pseudomonas* such as *Pseudomonas putida, Pseudomonas diminuta,* or *Pseudomonas mendocina,* a microorganism belonging to the genus *Rhodococcus* such as *Rhodococcus globerulus, Rhodococcus erythropolis, Rhodococcus rhodochrous,* or *Rhodococcus* sp., and a microorganism belonging to the genus *Bacillus* such as *Bacillus alvei*. Preferred examples include microbial cells or treated materials of a microorganism belonging to the genus *Rhodococcus* such as *Rhodococcus globerulus, Rhodococcus erythropolis, Rhodococcus rhodochrous,* or *Rhodococcus* sp. Further preferred examples include microbial cells or treated materials of a microorganism belonging to the genus *Rhodococcus* such as *Rhodococcus rhodochrous,* or *Rhodococcus* sp.

Specific examples thereof include microbial cells or treated materials of a microorganism of *Pseudomonas putida* IFO14164t, *Pseudomonas putida* IAM1236, *Pseudomonas diminuta* JCM2788t, *Pseudomonas mendocina* IFO14162, *Rhodococcus globerulus* ATCC15076, *Rhodococcus erythropolis* IFO12320, *Rhodococcus rhodochrous* ATCC15610, *Rhodococcus* sp. ATCC19148, or *Bacillus alvei* IFO3343t, which is cultured in the presence of water. Preferred examples include microbial cells or treated materials of a microorganism of *Rhodococcus globerulus* ATCC15076, *Rhodococcus erythropolis,* IFO12320, *Rhodococcus rhodochrous* ATCC15610, or *Rhodococcus* sp. ATCC19148, and further preferred examples include microbial cells or treated materials of a microorganism of *Rhodococcus rhodochrous* ATCC15610 or *Rhodococcus* sp. ATCC19148, which is cultured in the presence of water.

According to the process of the present invention, the carboxyl group of sulfur-containing ketol represented by the formula (1) can be reduced, and the hydroxyl group can be preferentially oxidized. The "preferentially oxidized" used herein means that the oxidation of the primary hydroxyl group preferentially progresses as compared with sulfide oxidation of the sulfur-containing ketol.

The microorganism belonging to the genus *Pseudomonas* such as *Pseudomonas putida, Pseudomonas diminuta,* or *Pseudomonas mendocina,* the microorganism belonging to the genus *Rhodococcus* such as *Rhodococcus globerulus, Rhodococcus erythropolis, Rhodococcus rhodochrous,* or *Rhodococcus* sp., or the microorganisms belonging to the genus *Bacillus* such as *Bacillus alvei,* which is used in the present invention, can be cultured using a culture medium for culturing various microorganisms, which appropriately contain a carbon source, a nitrogen source, an organic salt, an inorganic salt, and the like.

Examples of the carbon source contained in the culture medium include glucose, sucrose, glycerol, starch, alcohol, organic acid and molasses. As alcohols, particularly, primary or secondary alcohols having 1 to 5 carbon atoms are preferred, and examples thereof include methanol, ethanol, 1-propanol, 2-propanol, 1-butanol, 2-methyl-1-propanol, and 2,2-dimethyl-1-propanol. By culturing the above microorganism in a culture medium to which an alcohol is added, reactivity can be enhanced. Examples of the nitrogen source include yeast extract, meat extract, peptone, casamino acid, malt extract, soybean powder, corn steep liquor, cotton seed powder, dry yeast, ammonium sulfate and sodium nitrate, and examples of the organic salt and the inorganic salt include sodium chloride, potassium chloride, sodium carbonate, monopotassium phosphate, dipotassium phosphate, calcium carbonate, ammonium acetate, magnesium sulfate, copper sulfate, zinc sulfate, ferrous sulfate and cobalt chloride.

Examples of the culture method include solid culture, and liquid culture (test tube culture, flask culture, jar fermentor culture, etc.).

The culture temperature and a pH of a liquid culture medium are not particularly limited as far as they are in such a range that the microorganism to be used in the present invention can be grown. For example, the culture temperature is usually in a range of about 15 to 45° C., and the pH of a liquid culture medium is usually in a range of about 4 to 8. The culture time can be appropriately selected depending on culture conditions, and is usually about 1 to 7 days.

The cultured microbial cells can be used as such in the process of the present invention. For using microbial cells as such, for example, (1) a cultured liquid medium can be used as such or (2) microbial cells are collected by centrifugation of a cultured liquid medium, followed by using the collected cells (if necessary, as wet cells after washing with buffer or water).

Alternatively, in the process of the present invention, a treated material of the microbial cells obtained as described above can be used. Examples of the treated material include microbial cells treated with an organic solvent (e.g., acetone, ethanol, etc.) after culture thereof, microbial cells subjected to lyophilization treatment or alkali treatment, physically or enzymatically disrupted microbial cells, or crude enzymes separated and extracted from these treated materials. Further, the treated material includes an immobilized material of the aforementioned treated material prepared by a known method.

The process of the present invention is usually performed in the presence of water. In this case, water may be in a form of a buffer. Examples of a buffering agent used in the buffer include alkali metal salts of phosphoric acid such as sodium phosphate, potassium phosphate, etc., and alkali metal salts of acetic acid such as potassium acetate, etc.

Alternatively, the process of the present invention can be performed in the presence of water and a hydrophobic organic solvent. Examples of the hydrophobic organic solvent to be used include esters such as ethyl formate, ethyl acetate, propyl acetate, butyl acetate, ethyl propionate, butyl propionate, etc., alcohols such as n-butyl alcohol, n-amyl alcohol, n-octyl alcohol, etc., aromatic hydrocarbons such as benzene, toluene, xylene, etc., ethers such as diethyl ether, diisopropyl ether, methyl-t-butyl ether, etc., and halogenated hydrocarbons such as chloroform, 1,2-dichloroethane, etc., as well as a mixture thereof.

Further, the process of the present invention can also be performed in the presence of water and a hydrophilic organic solvent. Examples of the hydrophilic organic solvent to be used include alcohols such as methanol, ethanol, etc., ketones such as acetone, etc., and ethers such as diethoxymethane, tetrahydrofuran, dioxane, etc., as well as a mixture thereof.

The process of the present invention is usually performed in a range of a pH of the aqueous layer of 3 to 10, but the pH may be appropriately changed in such a range that the reaction proceeds.

The process of the present invention is usually performed in a range of about 0 to 60° C., but the temperature may be appropriately changed in such a range that the reaction proceeds.

The process of the present invention is usually performed in a range of for about 0.5 hour to about 10 days. The endpoint of the reaction can be confirmed by, after completion of addition of the starting material, i.e., the sulfur-containing ketol, measuring the amount of the sulfur-containing ketol in the reaction mixture by, for example, liquid chromatography, gas chromatography or the like.

The concentration of the starting material, i.e., the sulfur-containing ketol in the process of the present invention is usually not higher than 50% (w/v), and the sulfur-containing ketol can be continuously or sequentially added to a reaction system in order to maintain a concentration of the sulfur-containing ketol in the reaction system almost constant.

In the process of the present invention, if necessary, for example, a sugar such as glucose, sucrose, fructose, etc., a surfactant such as Triton X-100 (registered trade mark), Tween 60 (registered trade mark), etc. can be added to a reaction system.

After completion of the reaction, the objective sulfur-containing hydroxycarboxylic acid compound corresponding to the sulfur-containing ketol can be recovered from a reaction mixture by performing conventional post-treatment such as extraction with an organic solvent and concentration. The recovered sulfur-containing hydroxycarboxylic acid compound can be further purified by column chromatography, distillation or the like, if necessary.

The process of the present invention will be explained in more detail below by way of Examples, but the process of the present invention is not limited to these Examples.

REFERENCE EXAMPLE 1

Synthesis of 4-methylthio-2-oxo-1-butanol

A 200 mL flask equipped with a magnetic stirrer was charged with 23.7 g of 3-methylthiopropionaldehyde, 17.7 g of paraformaldehyde, 4 g of 3-ethylbenzothiazolinyl bromide and 100 g of tert-butanol at a room temperature, and the mixture was stirred. To this mixture was added 1.3 g of triethylamine, a temperature was raised to an internal temperature of 80° C., and the mixture was stirred at the same temperature for 24 hours. After completion of the reaction, 100 g of ethyl acetate was added, the mixture was washed twice with 20 g of water, and the resulting organic layer was concentrated. The resulting oil was distilled under reduced pressure, 15 g of 3-methylthiopropioaldehyde was recovered as a fraction at a distillation temperature of 45 to 50° C. (0.5 to 0.6 kPa), and 15 g of a fraction (hereinafter, fraction A) at a distillation temperature of 85 to 95° C. (0.3 kPa) was obtained. When the fraction A was analyzed by a gas chromatography area percentage method, 4-(methylthio)-2-oxo-1-butanol was contained at concentration of 40%. The fraction A was further purified by a silica gel column. After low polar impurities were expelled by elution with ethyl acetate: n-hexane=1:4, 4-(methylthio)-2-oxo-1-butanol was eluted with ethyl acetate:n-hexane=2:4. The solvent was distilled off to obtain 1.4 g of a fraction of 4-(methylthio)-2-oxo-1-butanol having a purity of 91% (gas chromatography area percentage method) and 2.0 g of a fraction having a purity of 82% (gas chromatography area percentage method). These fractions were all solidified at a room temperature. Spectral data of 4-(methylthio)-2-oxo-1-butanol $^1$H-NMR ($\delta_{ppm}$, DMSO-$d_6$, TMS standard): 2.05 (s, 3H), 2.62 (m, 2H), 2.70 (m, 2H), 4.06 (s, 2H), 5.13 (bs, 1H)

MS, m/z (relative intensity): 134 (32, M$^+$), 106 (20), 103 (19), 86 (5), 75 (55), 61 (100)

EXAMPLE 1

Production of Sulfur-Containing Hydroxycarboxylic Acid Compound from Sulfur-Containing Ketol According to the Process of the Present Invention Into a test tube was placed 5 ml of a sterilized medium (obtained by adding 20 g of 1-propanol, 5 g of polypeptone, 3 g of yeast extract, 3 g of meet extract, 0.2 g of ammonium sulfate, 1 g of potassium dihydrogen phosphate and 0.5 g of magnesium sulfate heptahydrate to 1 L of water, and then adjusting pH to 7.0), and the medium was inoculated with ATCC15610 strain belonging to *Rhodococcus rhodochrous*. The inoculated medium was shaking-cultured at 30° C. under aerobic conditions. After completion of the culture, microbial cells were separated by centrifugation to obtain live microbial cells. Into a screw-opening test tube was placed 1 ml of a 0.1 M potassium phosphate buffer (pH 7), the live microbial cells were added thereto to prepare a suspension. To the suspension was added 1 mg of a starting material (4-methylthio-2-oxo-1-butanol), and then the resulting mixture was shaken at 30° C. for 7 days.

After completion of the reaction, 0.5 ml of the reaction mixture was sampled. After microbial cells were removed from the sample mixture, the amount of 2-hydroxy-4-methylthiobutyric acid produced was analyzed by liquid chromatography. As a result, the concentration of the 2-hydroxy-4-methylthiobutyric acid produced was 0.75 g/L.

Content Analysis Conditions
Column: Cadenza CD-C18 (4.6 mmf×15 cm, 3 μm) (manufactured by Imtakt)
Mobile phase: 0.1% aqueous trifluoroacetic acid as A solution, methanol as B solution

| Time (min) | A solution (%) | B solution (%) |
|---|---|---|
| 0 | 80 | 20 |
| 10 | 80 | 20 |
| 20 | 50 | 50 |
| 30 | 50 | 50 |
| 30.1 | 80 | 20 |

Flow rate: 0.5 ml/min
Column temperature: 40° C.
Detection: 220 nm

EXAMPLE 2

Production of Sulfur-Containing Hydroxycarboxylic Acid Compound from Sulfur-Containing Ketol According to the Process of the Present Invention Into a test tube was placed 5 ml of a sterilized medium (obtained by adding 20 g of 1-propanol, 5 g of polypeptone, 3 g of yeast extract, 3 g of meat extract, 0.2 g of ammonium sulfate, 1 g of potassium dihydrogen phosphate and 0.5 g of magnesium sulfate heptahydrate to 1 L of water, and then adjusting pH to 7.0), and the medium was inoculated with ATCC19148 strain belonging to *Rhodococcus* sp. The inoculated medium was shaking-cultured at 30° C. under the aerobic condition. After completion of the culture, microbial cells were separated by centrifugation to obtain live microbial cells. Into a screw-opening test tube was placed 1 ml of a 0.1 M potassium phosphate buffer (pH 7), the live microbial cells were added thereto to prepare a suspension. To the suspension was added 1 mg of a starting material (4-methylthio-2-oxo-1-butanol), and then the resulting mixture was shaken at 30° C. for 7 days.

After completion of the reaction, 0.5 ml of the reaction mixture was sampled. After microbial cells were removed from the sample mixture, the amount of 2-hydroxy-4-methylthiobutyric acid produced was analyzed by liquid chromatography. As a result, the concentration of the 2-hydroxy-4-methylthiobutyric acid produced was 0.43 g/L.

Content Analysis Conditions

Column: Cadenza CD-C18 (4.6 mmf×15 cm, 3 μm) (manufactured by Imtakt)

Mobile phase: 0.1% aqueous trifluoroacetic acid solution as A solution, methanol as B solution

| Time (min) | A solution (%) | B solution (%) |
|---|---|---|
| 0 | 80 | 20 |
| 10 | 80 | 20 |
| 20 | 50 | 50 |
| 30 | 50 | 50 |
| 30.1 | 80 | 20 |

Flow rate: 0.5 ml/min

Column temperature: 40° C.

Detection: 220 nm

EXAMPLE 3

Production of Sulfur-Containing Hydroxycarboxylic Acid Compound from Sulfur-Containing Ketol According to the Process of the Present Invention Into a test tube was placed 5 ml of a sterilized medium (obtained by adding 20 g of glucose, 5 g of polypeptone, 3 g of yeast extract, 3 g of meat extract, 0.2 g of ammonium sulfate, 1 g of potassium dihydrogen phosphate and 0.5 g of magnesium sulfate heptahydrate to 1 L of water, and then adjusting pH to 7.0), and the medium was inoculated with IFO3343t strain belonging to *Bacillus alvei*. The inoculated medium was shaking-cultured at 30° C. under aerobic conditions. After completion of the culture, microbial cells were separated by centrifugation to obtain live microbial cells. Into a screw-opening test tube was placed 1 ml of a 0.1 M potassium phosphate buffer (pH 7), the live microbial cells were added thereto to prepare a suspension. To the suspension was added 1 mg of a starting material (4-methylthio-2-oxo-1-butanol), and then the resulting mixture was shaken at 30° C. for 10 days.

After completion of the reaction, 0.5 ml of the reaction mixture was sampled. After microbial cells were removed from the sample mixture, the amount of 2-hydroxy-4-methylthiobutyric acid produced was analyzed by liquid chromatography. As a result, the concentration of the 2-hydroxy-4-methylthiobutyric acid produced was 0.03 g/L.

Content Analysis Conditions

Column: Cadenza CD-C18 (4.6 mmf×15 cm, 3 μm) (manufactured by Imtakt)

Mobile phase: 0.1% aqueous trifluoroacetic acid solution as A solution, methanol as B solution

| Time (min) | A solution (%) | B solution (%) |
|---|---|---|
| 0 | 80 | 20 |
| 10 | 80 | 20 |
| 20 | 50 | 50 |
| 30 | 50 | 50 |
| 30.1 | 80 | 20 |

Flow rate: 0.5 ml/min

Column temperature: 40° C.

Detection: 220 nm

EXAMPLE 4

Production of Sulfur-Containing Hydroxycarboxylic Acid Compound from Sulfur-Containing Ketol According to the Process of the Present Invention Into a test tube was placed 5 ml of a sterilized medium (obtained by adding 20 g of 1-propanol, 5 g of polypeptone, 3 g of yeast extract, 3 g of meat extract, 0.2 g of ammonium sulfate, 1 g of potassium dihydrogen phosphate and 0.5 g of magnesium sulfate heptahydrate to 1 L of water, and then adjusting pH to 7.0), and the medium was inoculated with each of *Pseudomonas putida* IFO14164t, *Pseudomonas putida* IAM1236, *Pseudomonas diminuta* JCM2788t, *Pseudomonas mendocina* IFO14162, *Rhodococcus globerulus* ATCC15076, and *Rhodococcus erythropolis* IFO12320 strains. Each inoculated medium was shaking-cultured at 30° C. under aerobic conditions. After completion of the culture, microbial cells were separated by centrifugation to obtain live microbial cells. Into a screw-opening test tube was placed 1 ml of a 0.1 M potassium phosphate buffer (pH 7), the live microbial cells were added thereto to prepare a suspension. To the suspension was added 1 mg of a starting material (4-methylthio-2-oxo-1-butanol), and then the resulting mixture was shaken at 30° C. for 5 days, or 10 days.

After completion of the reaction, 0.5 ml of the reaction mixture was sampled. After microbial cells were removed from the sample mixture, the amount of 2-hydroxy-4-methylthiobutyric acid produced was analyzed by liquid chromatography. The results are shown in Table 1.

TABLE 1

| Strain | Reaction time (days) | Concentration of 2-hydroxy-4-methylthiobutyric acid produced (g/L) |
|---|---|---|
| *Pseudomonas putida* IFO14164t | 10 | 0.43 |
| *Pseudomonas putida* IAM1236 | 5 | 0.27 |
| *Pseudomonas diminuta* JCM2788t | 10 | 0.45 |
| *Pseudomonas mendocina* IFO14162 | 10 | 0.25 |

TABLE 1-continued

| Strain | Reaction time (days) | Concentration of 2-hydroxy-4-methylthiobutyric acid produced (g/L) |
|---|---|---|
| *Rhodococcus globerulus* ATCC15076 | 5 | 0.02 |
| *Rhodococcus erythropolis* IFO12320 | 5 | 0.05 |

Content Analysis Conditions

Column: Cadenza CD-C18 (4.6 mmf×15 cm, 3 μm) (manufactured by Imtakt)

Mobile phase: 0.1% aqueous trifluoroacetic acid solution as

A solution, methanol as B solution

| Time (min) | A solution (%) | B solution (%) |
|---|---|---|
| 0 | 80 | 20 |
| 10 | 80 | 20 |
| 20 | 50 | 50 |
| 30 | 50 | 50 |
| 30.1 | 80 | 20 |

Flow rate: 0.5 ml/min
Column temperature: 40° C.
Detection: 220 nm

INDUSTRIAL APPLICABILITY

According to the present invention, a sulfur-containing hydroxycarboxylic acid compound can be efficiently produced.

The invention claimed is:

1. A process for producing a sulfur-containing α-hydroxycarboxylic acid compound represented by the formula (2):

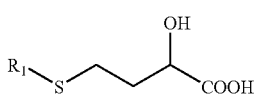
(2)

wherein $R_1$ represents a hydrogen atom, an alkyl group having 1 to 8 carbon atoms, or an aryl group having 6 to 20 carbon atoms, which comprises subjecting a sulfur-containing ketol represented by the formula (1):

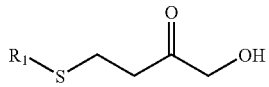
(1)

wherein $R_1$ is the same as defined above, to the action of microbial cells of *Rhodococcus* sp. ATCC19148 or a microorganism belonging to *Pseudomonas putida, Pseudomonas diminuta, Pseudomonas mendocina, Rhodococcus globerulus, Rhodococcus erythropolis, Rhodococcus rhodochrous,* or *Bacillus alvei* capable of converting the sulfur-containing ketol into a corresponding sulfur-containing α-hydroxycarboxylic acid compound, or a treated material thereof, wherein the treated material is selected from the group consisting of microbial cells treated with an organic solvent after culture thereof, microbial cells subjected to lyophilization treatment or alkali treatment, physically or enzymatically disrupted microbial cells, crude enzymes separated and extracted from these treated materials, and immobilized material of these treated materials.

2. The process according to claim 1, wherein the microorganism is *Rhodococcus* sp. ATCC19148 or that belonging to *Pseudomonas putida, Pseudomonas diminuta, Pseudomonas mendocina, Rhodococcus globerulus, Rhodococcus erythropolis* or *Rhodococcus rhodochrous* which has been cultured in the presence of a primary or secondary alcohol.

3. The process according to claim 2, wherein the primary or the secondary alcohol is a primary or secondary alcohol having 1 to 5 carbon atoms.

4. The process according to claim 3, wherein the primary or the secondary alcohol is 1-propanol.

5. The process according to claim 1, wherein the microorganism is that belonging to *Bacillus alvei*.

6. The process according to claim 1, wherein the microorganism is *Pseudomonas putida* IFO14164t, *Pseudomonas putida* IAM1236, *Pseudomonas diminuta* JCM2788t, *Pseudomonas mendocina* IFO14162, *Rhodococcus globerulus* ATCC15076, *Rhodococcus erythropolis* IFO12320, *Rhodococcus rhodochrous* ATCC 15610, or *Rhodococcus* sp. ATCC 19148.

7. The process according to claim 1, wherein the microorganism is *Bacillus alvei* IFO3343t.

8. The process according to claim 1, wherein $R_1$ in the sulfur-containing ketol represented by the formula (1) is an alkyl group having 1 to 8 carbon atoms.

* * * * *